United States Patent [19]

Petty et al.

[11] 4,252,522
[45] Feb. 24, 1981

[54] DENTAL MIRROR WITH ENDODONTIC FILE MEASURING SURFACE

[76] Inventors: Marshall K. Petty; Marsha L. Goodmon, both of 317 Robinson Bldg., Miami, Okla. 74354

[21] Appl. No.: 26,298
[22] Filed: Apr. 2, 1979
[51] Int. Cl.³ .............................................. A61B 1/24
[52] U.S. Cl. .......................................... 433/30; 433/75
[58] Field of Search ............................ 433/30, 31, 75

[56] References Cited

U.S. PATENT DOCUMENTS 3,388,473  6/1968  Loran ...................................... 433/75
3,855,705  12/1974  Malmin ................................... 433/32
4,028,810  6/1977  Vice ........................................ 433/75

FOREIGN PATENT DOCUMENTS 1810933  6/1970  Fed. Rep. of Germany ............. 433/30

Primary Examiner—Gene Mancene
Assistant Examiner—John J. Wilson
Attorney, Agent, or Firm—Head & Johnson

[57] ABSTRACT

A dental mirror includes at its handle end a depressed surface having indicia markings thereon for measuring endodontic file or reamer depths.

2 Claims, 3 Drawing Figures

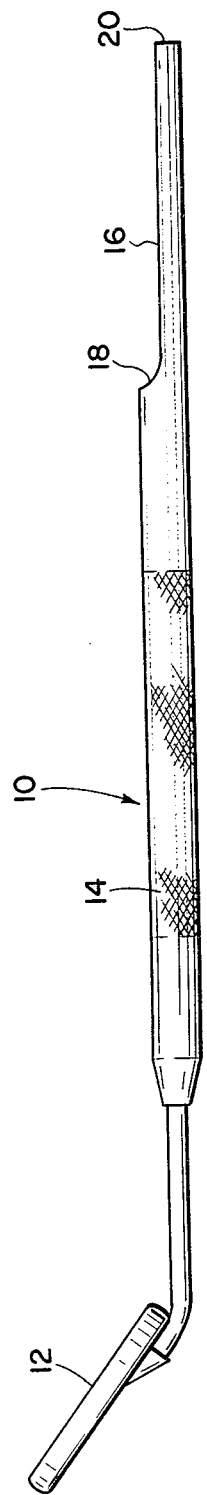
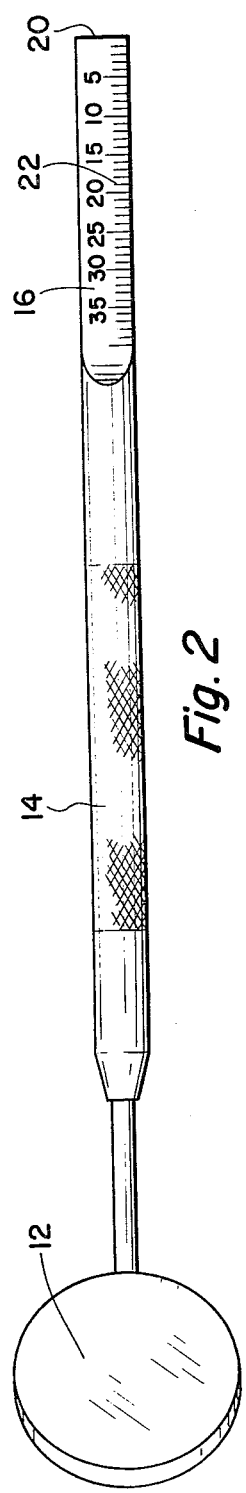
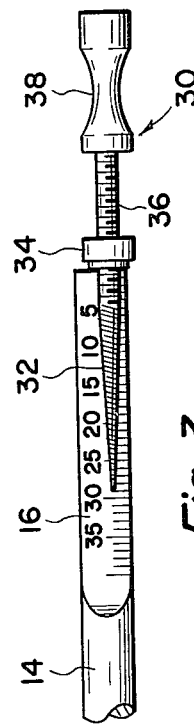
Fig. 1
Fig. 2
Fig. 3

DENTAL MIRROR WITH ENDODONTIC FILE MEASURING SURFACE

BACKGROUND OF THE INVENTION

This invention is in the field of dentistry. In the filing or reaming of the root canals of endodontically involved teeth, it is important to limit the depth of penetration of the file or reamer used to avoid injury. A typical file includes an adjustable depth stop. During such treatments there are often interruptions to make the accurate determination and control over the depth to which the file or reamer is to be inserted. The dentist must oftentimes stop, make a depth determination or adjustment from other measuring instruments and then return to the treatment. This is time-consuming and inefficient. Such endodontic measurement systems and tools are shown, for example, in the following U.S. Pat. Nos.:

3,562,913 Saffro
3,713,221 Malmin
3,855,705 Malmin

SUMMARY OF THE INVENTION

This invention is directed to providing at the handle end of a typical dental mirror a recessed and graduated indicia surface by which the dentist may make simple and accurate measurements of the depth of the reaming tool without stopping and interrupting the operational procedure and treatment as has been heretofore known in the art.

The invention is directed to typical angle-type dental mirror, having a handle portion, the end of which is curvably recessed to a flat surface with indicia thereon. The end of the dental mirror terminates in a 90° surface to the notched recessed flat surface. The flat surface including measuring marks thereon, e.g. millimeter graduation.

BRIEF DESCRIPTION OF THE DRAWINGS

FIG. 1 is a side view of the apparatus comprising the invention.

FIG. 2 is a top view of the device of FIG. 1.

FIG. 3 is a partial sectional top view showing the invention in use with a typical root canal file.

DETAILED DESCRIPTION OF THE INVENTION

Before explaining the present invention in detail, it is to be understood that the invention is not limited in its application to the details of construction and arrangement of parts illustrated in the accompanying drawings since the invention is capable of other embodiments and of being practiced or carried out in a variety of ways. Also, it is to be understood that the phraseology or terminology employed herein is for the purpose of description and not of limitation.

Referring now to the drawings, the numeral 10 generally indicates the apparatus of this invention, which is a typical dentist mirror having an angled mirror portion 12, a handle portion 14. The end of the handle has a flat recessed surface 16 extending from a curved portion 18 to the end 20 which is to be 90° to the flat surface 16. Suitably etched and/or otherwise marked on the top of the surface 16 are millimeter or other indicia graduations 22, which are utilized by the dentist in adjusting the depth of the file or reamer used in the endodontic treatment. In use, the mirror, which is usually held by an assistant or the dentist during the treatment is conveniently in position without undue movement to expose the surface 16 for positioning a reamer or file tool, generally designated as 30 in FIG. 3. The file includes a tapered file portion 32 and an i.e. threaded adjustable depth stop 34, is rotated upon a threaded portion 36. An appropriate handle 38 is provided.

The objective of the operation is to determine and control the depth to which the file or reamer is inserted. This may be accomplished with this invention by abutting the depth stop 34 against the end 20 so that the reamer is positioned atop the indicia 22 of surface 16. The reamer or file is placed into the canal, adjusting the depth stop, so as to be in contact with an anatomical landmark on the surface of the tooth, and taking an x-ray to determine the relationship of the tip of the instrument to the apex of the root. Once the correct instrument length has been determined, the succeeding instruments must be "stopped" from penetrating to any depth greater than determined as ideal by the dentist. The fact that the adjustments can be accomplished using the recessed surface at the end of the dentist's mirror handle as taught in this invention greatly saves time and effort by the dentist and inconvenience to the patient.

It is claimed:

1. In a dental mirror angularly placed at one end of a rod-like handle portion, the improvement characterized by an indentation within the confines of the rod-like handle beginning from an inwardly curved surface to a flat surface having measuring graduations thereon to the other end surface which is 90° to the flat surface whereby a depth stop on a dental file or reamer can be abutted against said 90° end surface so that the file or reamer is positioned atop said graduations, and whereby the depth of said file or reamer can be measured and adjusted for use in endodontic treatment.

2. The device of claim 1, the further improvement in the graduation being millimeter indicia.

* * * * *